(12) United States Patent
Combe et al.

(10) Patent No.: US 6,419,904 B1
(45) Date of Patent: Jul. 16, 2002

(54) FLAVORED TOOTH CONDITIONING COMPOSITIONS AND METHODS FOR USING THE COMPOSITIONS TO CONDITION A TOOTH SURFACE

(75) Inventors: Edward C. Combe, Maplewood, MN (US); John H. Warford, III; John H. Warford, II, both of Bismarck, ND (US)

(73) Assignee: Dakota Dental Development, Inc., Bismarck, ND (US)

(*) Notice: Subject to any disclaimer, the term of this patent is extended or adjusted under 35 U.S.C. 154(b) by 0 days.

(21) Appl. No.: 09/944,824

(22) Filed: Aug. 31, 2001

Related U.S. Application Data

(62) Division of application No. 09/427,943, filed on Oct. 27, 1999, now Pat. No. 6,342,204.

(51) Int. Cl.[7] ............................................... A61K 7/16
(52) U.S. Cl. ......................... 424/49; 424/57; 433/216
(58) Field of Search ..................... 424/49, 57; 433/216, 433/226, 228.1

(56) References Cited

U.S. PATENT DOCUMENTS

| 3,943,949 A | 3/1976 | Ashton et al. |
| 4,182,035 A | 1/1980 | Yamauchi et al. |
| 4,222,780 A | 9/1980 | Shibatani et al. |
| 4,235,633 A | 11/1980 | Tomioka et al. |
| 4,259,075 A | 3/1981 | Yamauchi et al. |
| 4,259,117 A | 3/1981 | Yamauchi et al. |
| 4,374,822 A | 2/1983 | Fine et al. |
| RE31,954 E | 7/1985 | Fine et al. |
| 4,669,983 A | 6/1987 | Bunker |
| 4,710,217 A | 12/1987 | Bailey et al. |
| 4,738,722 A | 4/1988 | Ibsen et al. |
| 4,758,163 A | 7/1988 | Goldman |
| 4,773,933 A | 9/1988 | Futami et al. |
| 5,015,180 A | 5/1991 | Randklev |
| 5,051,130 A | 9/1991 | Futami et al. |
| 5,063,257 A | 11/1991 | Akahane et al. |
| 5,073,363 A | 12/1991 | Pellico |
| 5,130,122 A | 7/1992 | Tabibi et al. |
| 5,154,613 A | 10/1992 | Cohen |
| 5,177,121 A | 1/1993 | Bunker |
| 5,256,065 A | 10/1993 | Nicholson |
| 5,522,725 A | 6/1996 | Jordan et al. |
| 5,554,030 A | 9/1996 | Ario et al. |
| 5,575,645 A | 11/1996 | Jacobs et al. |
| 5,595,487 A | 1/1997 | Ario et al. |
| 5,639,239 A | 6/1997 | Earle |
| 5,645,429 A | 7/1997 | Blackwell et al. |
| 5,662,886 A | 9/1997 | Oxman et al. |
| 5,696,181 A | 12/1997 | Chang et al. |
| 5,708,052 A | 1/1998 | Fischer et al. |
| 5,711,665 A | 1/1998 | Adam et al. |
| 5,756,559 A | 5/1998 | Blackwell et al. |
| 5,766,012 A | 6/1998 | Rosenbaum et al. |
| 5,900,230 A | 5/1999 | Cutler |
| 5,932,627 A | 8/1999 | Blackwell |
| 6,036,494 A * | 3/2000 | Cohen ..................... 433/217.1 |
| 6,342,204 B1 * | 1/2002 | Combe et al. ................ 424/49 |

FOREIGN PATENT DOCUMENTS

DE   197 22 596   3/1998

OTHER PUBLICATIONS

O'Brien, "Dental Materials and Their Selection," Appendix A, p. 332, 1997.
Sano et al., "Relationship between surface area for adhesion and tensile bond strength–Evaluation of a micro–tensile bond test," Dental Materials, Jul. 1994, pp. 236–240.
Aboush Y., Resin to Enamel Bonds, British Dental J 171 (7)207–209, Jul. 1991.
Chan A., A Short and Long Term Shear Bond Strength Study Using Acids of Varying Dilutions on Bovine Dentine, J. of Dentistry 25(2) 145–452, Feb. 1997.

* cited by examiner

Primary Examiner—Ralph Gitomer
(74) Attorney, Agent, or Firm—Kagan Binder, PLLC

(57) ABSTRACT

Compositions for conditioning a tooth surface prior to the application of a dental materials which will desirably form a substantially permanent bond with the conditioned tooth surface are provided. The conditioning compositions comprise an amount of an essential oil effective to alter the sensory properties, i.e. the taste, a smell, of the conditioning composition and that desirably imparts a more pleasing taste and/or odor. Also provided are methods of using the conditioning composition to prepare a tooth surface for the application of a free radically polymerizable dental material and for treating a tooth by forming a substantially permanent bond with a free radically polymerizable dental material.

19 Claims, No Drawings

FLAVORED TOOTH CONDITIONING COMPOSITIONS AND METHODS FOR USING THE COMPOSITIONS TO CONDITION A TOOTH SURFACE

REFERENCE TO RELATED APPLICATIONS

This is a division of application Ser. No. 09/427,943 Oct. 27, 1999, now U.S. Pat. No. 6,342,204.

FIELD OF THE INVENTION

This invention relates to compositions for preparing or conditioning a tooth surface, i.e., enamel and/or dentin, for one or more dental procedures intended to repair, adhere to, or alter the position of, the tooth. In particular, the present invention relates to conditioning compositions that comprise an amount of oil that can be effective to alter, i.e., reduce, eliminate or improve, the sensory properties of the conditioning composition. The invention also relates to methods of utilizing the conditioning compositions to prepare a tooth surface for one or more dental procedures.

BACKGROUND OF THE INVENTION

Significant advancements have been made in the field of dentistry in recent years; many in efforts to render dental procedures more comfortable for the patient. Patient comfort is not only important to the individual patient being treated, but also to the dental professional performing the treatment. Particularly in that instance when the patient is a child, a patient that is comfortable and relaxed is much less likely to move in a manner so as to make the treatment more difficult for the dental professional to perform. Additionally, a comfortable patient is more likely to take the direction of the dental professional during the treatment, and further, to adhere to any prescribed regimens post-treatment. However, although many new materials and/or procedures have been provided, or existing materials and procedures improved, that enhance patient comfort, i.e., such as improvements in anesthetic materials and the development of more comfortable tooth preparation procedures, there still exist areas within the field of dentistry in which patient comfort could be further enhanced or optimized.

Many patients visit dentists to have various materials adhered to their teeth in order to repair or replace otherwise damaged tooth tissue, to alter the position of the teeth, to provide prophylactic therapy, i.e., to aid in the prevention of decay, or in some instances, for cosmetic purposes. Such materials include oral rehabilitative materials such as inlays, crowns and bridges; oral restoration materials; orthodontic brackets; pit and fissure sealants; cosmetic materials such as veneers, and the like. In each of these, and in fact all dental applications in which materials are desirably permanently bonded to tooth structure, the integrity of the bond between the tooth and the applied material is crucial to the success of the treatment.

In order to enhance the integrity of such bonds, the surface of the tooth, and specifically, the enamel or dentin, is typically prepared in a manner that will later enhance the ability of the desired material to bond to the enamel and/or dentin. Generally, such preparation is carried out via the application of an acidic material, referred to as an etchant when the material is to be applied to enamel and as a conditioner when the material is to be applied to dentin. The materials will hereinafter collectively be referred to as "conditioners" or "conditioning components." In the case of enamel, these materials selectively decalcify tooth substance, producing a roughened surface capable of interacting with the desired material in a mechanical manner thereby enhancing the bond strength between the roughened tooth structure and the material to be adhered. In the case of dentin, the conditioner removes the "smear layer" of dentin and an amount of hydroxyapatite, leaving exposed collagen. The desired material to be adhered is then capable of forming a "hybrid layer" with the so-exposed collagen, thereby firmly bonding the desired material to the tooth.

Although extremely effective at preparing a tooth surface to firmly and permanently bond with a dental material, many, if not most, of the conditioners used for this purpose have the undesirable quality of having an unpleasant taste, generally due to their acidic nature. This unpleasant taste can result in patient discomfort that can manifest itself in the patients noncompliance with requests or instructions, movement that can make the treatment difficult to perform, and other behavior belying emotional distress on the part of the patient.

In order to enhance the patient's experience, and in keeping with the general trend of making dentistry more acceptable for patients, it would be desirable to at least reduce or eliminate the unpleasant flavor associated with conventional conditioning materials, and would be even more desirable to provide such materials with a pleasant flavor while also beneficially imparting such materials with a pleasing aroma. That is, where the use of conventionally unpleasant tasting conditioning materials could potentially result in the patient having a negative experience, the use of such materials with a pleasant flavor and odor could greatly enhance the patient's experience. Particularly in the instance of children, the ability to choose a flavored material which they find pleasing can be a positive psychological experience that may result in better behavior during the treatment as well as the enhanced future compliance with instructions. Additionally, it is a well known concept in dentistry to increase patient compliance and interest by involving the patient in treatment decisions.

Unfortunately, there has not been provided in the field of dentistry effective conditioning materials with either no, or more preferably a pleasant, flavor and also beneficially with a pleasing aroma. Most probably this is a result of the fact that such conditioning materials desirably leave the treated tooth surface substantially free of contaminants so that effective adhesion with the desired dental material may be achieved. That is, conventional dental knowledge teaches that a clean tooth surface is required in order for a bond with sufficient integrity to be relatively permanent to be formed between the conditioned tooth surface and the desired dental material. Inasmuch as most known flavoring materials, and in particular those provided as oils, are thought to leave residue behind on the tooth that could interfere with ability of the tooth surface to bond to the dental material with the integrity required, such materials have conventionally not been added to tooth conditioning materials, and in fact, their addition to these materials has been avoided.

It would thus be desirable to provide tooth conditioning materials with either no substantial flavor, or more preferably with a pleasant flavor. Such materials would desirably substantially retain their effectiveness as tooth conditioning materials and also would preferably not result in the deposition of a contaminant on the conditioned tooth surface that would substantially interfere with the ability of the conditioned tooth surface to form a bond with a subsequently applied dental material.

SUMMARY OF THE INVENTION

The present invention is drawn to tooth conditioning compositions that comprise an amount of an essential oil. In particular, the essential oil is preferably included in the tooth conditioning compositions in an amount effective to alter the sensory properties, i.e., flavor and/or odor, of the tooth conditioning composition. It has now been surprisingly discovered that by including such an essential oil in conventional tooth conditioning compositions, that the flavor and/or odor thereof can be altered to a degree so as to be rendered pleasant, but yet the inclusion of such an oil does not substantially interfere with the ability of the conditioned tooth surface to bond with a dental material with sufficient integrity so as to be substantially permanent.

Thus, in one aspect, the present invention provides a conditioning composition for use in dentistry comprising an essential oil in an amount effective to alter one or more of the sensory properties of the conditioning composition. While not wishing to be bound by any theory, it is believed that not only do the essential oils further defined and identified hereinbelow as being suitable for use in the present invention not substantially interfere with free radical polymerization, a method of action by which many dental materials harden, or cure, but that these oils are also actually compatible with these types of dental materials. Thus, the presence of some residual amount of these oils on the conditioned tooth surface will not substantially interfere with the ability of the conditioned tooth surface to form a substantially permanent bond with free radically polymerizable dental materials. This is a surprising and unexpected result inasmuch conventional dental knowledge teaches that any residue, and in particular oil residue, on a tooth surface after tooth conditioning is undesirable and to be avoided as it is understood to interfere with the ability of the dental material to effectively bond to the conditioned tooth.

Thus, in other aspects of the present invention, there are also provided compositions for use in dentistry, wherein the composition is used to condition a tooth surface prior to the application of a free-radically polymerizable dental material and furthermore, methods for preparing a tooth surface for the application of a free radically polymerizable dental material. Specifically, the method comprises the steps of applying a conditioning composition comprising an essential oil to the surface to which the free radically polymerizable dental restorative material is to be applied in an amount effective to etch at least a portion of the tooth surface, applying the free radically polymerizable dental restorative material to the etched tooth surface, and causing the free radically polymerizable dental restorative material to harden.

As used herein, the phrase "conditioning composition" is meant to indicate a composition that is used to prepare a tooth surface for a subsequent treatment in which a dental material is desirably adhered to the tooth, and in particular to indicate compositions that prepare a tooth surface by the removal of some amount of tooth material, i.e., either enamel or dentin. Also, as used herein, the phrase "substantially permanent" as it is used pertaining to the bond between the tooth (either enamel or dentin) and a dental material is meant to indicate a bond that is sufficiently strong and secure, so that the applied dental material will be a substantially permanent structure within the mouth, i.e., that at least at the time that the dental material is applied, the material is intended to remain adhered to the tooth structure indefinitely. Thus, the phrase "substantially permanent" does not exclude dental materials that, due to extenuating circumstances unrelated to the initial integrity of the bond, fail prematurely. Generally speaking, a shear bond strength of at least about 13 MPa, and preferably from about 15 MPa to about 35 MPa, is sufficiently strong so as to render dental materials adhered to tooth structure with this bond strength "substantially permanent." Bond strength method may be measured, for example, as described below in connection with Example 1. See also, e.g., William J. O'Brien, PhD, "Dental Materials and Their Selection," $2^{nd}$ ed., p. 332 (1997). It should be noted that higher bond strengths can be obtained using micro-testing methods such as those disclosed in Sano et al., "Relationship between surface area for adhesion and tensile bond strength—Evaluation of a micro-tensile bond test." Dent Mater 10:236, Jul., 1994.

Finally, the conditioning compositions in accordance with the present invention advantageously include an amount of an essential oil sufficient to alter one or more of the sensory properties, i.e. taste or smell, of the conditioning compositions. That is, the essential oil may simply act to ameliorate and otherwise unpleasant taste or odor, or desirably, may impart a more pleasing flavor and/or odor to the composition.

Unless otherwise indicated, as used herein, all references to percentages are percentages by weight of the conditioning composition.

DETAILED DESCRIPTION OF THE INVENTION

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

The present invention provides conditioning compositions for use in dentistry that comprise one or more essential oils. In particular, the essential oil(s) is/are desirably present in the conditioning composition in an amount effective to alter one or more of the sensory properties, i.e., the taste or smell, of the conditioning composition.

Conventional conditioning compositions generally have an unpleasant flavor that renders their use in the mouth a potentially unpleasant experience for many patients. The inclusion of agents in order to alter the flavor of these compositions has not previously been considered a viable solution to this problem, due to the fact that many flavoring agents have the undesirable affect of leaving some residue, in the form of particulate matter such as powder or oil, on the surface of the tooth treated thereby. Such residue is conventionally considered undesirable as it is thought to interfere with the ability of the conditioned tooth surface to form bonds with subsequently applied dental materials.

However, it has now been surprisingly discovered that the oils suitable for use in the present invention can be easily and conveniently incorporated into these conventional conditioning materials to either reduce any unpleasant taste, and in some instances, to provide these conventional conditioning materials with a pleasant taste and/or odor, without concurrently detrimentally affecting the ability of the tooth surface conditioned with these materials to adhere to later applied dental materials. In particular, it has now been found that certain oils do not interfere with free radical polymerization, and as a result, these oils can be utilized in conventional conditioning compositions since the presence of a residual amount of such oils on the conditioned tooth surface generally will not interfere with the ability of the conditioned tooth surface to bond to other dental materials that harden or cure via this mechanism, and in fact, such oils have been found to be substantially compatible with these types of dental materials.

The oils useful in the present invention are thus those oils which are capable of altering the sensory properties of conventional conditioning materials without detrimentally affecting the ability of the tooth surface to form substantially permanent bonds with other dental materials, i.e., that do not interfere with free radical polymerization, and which are orally nontoxic. Generally speaking, these qualities are embodied by "essential" oils, i.e., oils which are derived from plant sources or animal sources. Examples of such oils include, but are not limited to, soybean oil, safflower oil, sesame oil, olive oil, sunflower oil, canola oil, walnut oil, peanut oil, orange oil, eucalyptus oil, cod liver oil, castor oil, combinations thereof, and the like. Such oils are readily commercially available from a variety of sources as will be readily appreciated by one of ordinary skill in the art. Furthermore, inasmuch as these oils are generally consumable food items in reasonable quantity, oral toxicity is generally not a concern.

As used herein the phrase "conditioning composition" is meant to indicate a material used in the mouth to etch or condition the surface of a tooth, whether enamel or exposed dentin, ie., etchants and conditioners. Although there are many different types of each of these materials, e.g., compositions intended for the treatment of enamel, the treatment of dentin, or the treatment of both, the type of conditioning material into which the oil is to be incorporated is not particularly restricted, and in fact, it is believed that the oil may be mixed into many or all types of the aforementioned materials and provide the advantages disclosed herein.

Preferably, the conditioning composition into which the oil is incorporated is a material which acts to remove material from the surface of the tooth, e.g., a material that acts as an etchant of either enamel, dentin or both. Etchants typically remove material from the exposed tooth surface by virtue of the action of an amount of acid, and in particular, many of such etchants include an amount of phosphoric acid, in concentrations ranging from 10% to 40% by weight. Etchants may also include acids such as citric acid, poly (acrylic acid) or maleic acid. Such materials are well known to those of ordinary skill in the art and are readily commercially available. Examples of commercially available etchants include, but are not limited to Scotchbond Etchant (3M, St. Paul, Minn.); All-Etch (Bisco Dental, Schaumburg, Ill.); Citric-etch (Ellman, Hewlett, N.Y.); Copalite Dentin Conditioner (Cooley and Cooley, Houston, Tex.); Copalite Enamel Etch (Cooley and Cooley, Houston, Tex.); Dentin Conditioner (Scientific Pharmaceuticals. Pomona, Calif.), Etch 'N Seal (Den-Mat, Santa Maria, Calif.); Etch Gel 10% and Etch Gel 40% (Zenith Foremost, Englewood, N.J.); Etch 37 (Bisco Dental, Schaumburg, Ill.); Etch-All (Pulpdent, Watertown, Mass.); Etch-Rite (Pulpdent, Watertown, Mass.); Etcharrest (Ultradent Products, South Jordan, Utah); Etching Gel (Espe, Norristown, Pa.); Etching Gel Kit (Cosmedent, Chicago, Ill.); GC Cavity Conditioner (GC America, Alsip, Ill.); GC Dentin Conditioner (GC America, Alsip, Ill.); Gel Etch 10% Orthophosphoric acid (Scientific Pharmaceuticals, Pomona, Calif.); Gel Etch 33% Orthophosphoric acid (Scientific Pharmaceuticals, Pomona, Calif.); Gel-Etch (Temrex, Freeport, N.Y.); Gentle-Etch (Temrex, Freeport, N.Y.); Ketac Conditioner (Espe, Norristown, Pa.) Sigma Conditioner Gel (Global. Dental, North Bellmore, N.Y.); Star Etch Phosphoric Etchant (Danville Materials, San Ramon, Calif.), Super Etch Gel, (Southern Dental, San Francisco, Calif.); Tooth Conditioner (Dentsply Caulk, Milford, Del.); and Ultra-Etch (Ultradent Products, South Jordan, Utah).

The conditioning compositions of the present invention may readily and conveniently be prepared at a point of use by one of ordinary skill in the art by simply combining the desired essential oil with the desired conventional conditioning composition. Such combining may take place immediately prior to the use of the composition, or alternatively, the essential oil may be combined with the conventional conditioning composition and then stored until the use thereof is desired. If the conditioning composition is to be stored for a period of time, the conditions of storage are not substantially impacted by the inclusion of the essential oil, and thus conditioning composition in accordance with the present invention may be stored in the manner appropriate for the conventional conditioning composition.

The oil is desirably included in the conditioning composition in an amount that is effective to alter the sensory properties of the conditioning composition. As a lower limit, at least enough of the oil should be included so that the oil is capable of reducing any unpleasant flavor of the conditioning composition. As an upper limit, not So much oil should be included so that the properties or effectiveness of the tooth conditioning material are substantially detrimentally affected. Bearing these considerations in mind, and generally speaking, the amount of oil that is thought to achieve the aforementioned objectives will likely range from about 1 weight percent (wt %) to about 35 wt %, preferably from about 10 wt % to about 20 wt %, more preferably from about 13 wt % to about 17 wt %, based upon the total weight of the tooth conditioning material, including the oil.

Of course, the particular amount of oil that is to be included in the conditioning composition will be dependent upon the particular conventional conditioning composition and oil chosen. For exemplary purposes only, and in that embodiment of the invention wherein the conventional conditioning composition is Scotchbond Etchant and the oil is soybean oil, the oil is desirably included in the conventional conditioning material in an amount of from about 10% to about 20% to prepare one representative conditioning composition in accordance with the present invention.

Although it is contemplated that any of the essential oils listed above, or any other essential oil that does not substantially interfere with free radical polymerization, will be capable in some amount of at least minimizing the unpleasant flavor of, or imparting a pleasant flavor and/or odor to a conventional conditioning composition, in some instances it may be desirable to impart a stronger flavor or a particular flavor that is not readily available in an oil form. For example, children generally prefer sweeter and/or stronger flavors than adults and thus may prefer flavors such as cherry, strawberry, blueberry, watermelon, orange, lemon, lime raspberry, apple, grape, cranberry, coconut, caramel, banana, tangerine, pineapple, bubble gum, almond, hazelnut and the like, rather than spearmint or orange flavors. In these instances, the essential oil to be incorporated into the conditioning composition of the present invention may further have incorporated therein an amount of a flavoring agent such as those previously mentioned, i.e., the essential oil may act as a carrier for other flavoring agents. Such flavoring agents are readily commercially available as either syrups, solutions or solids, and may be incorporated into the essential oil simply by mixing the desired flavoring agent with the essential oil. Experiments have shown that the inclusion of such a flavoring agent in the essential oil will not have a detrimental effect on the bondability of a tooth surface prepared with a conditioning material including a combination of the essential oil and the flavoring agent.

The compositions of the present invention may optionally comprise other ingredients that may be used to further enhance the sensory and/or mechanical properties of the non-metallic compositions. For example, it has additionally been found that certain other liquids, such as glycerol or propylene glycol, can be used as carriers for the flavoring agents mentioned hereinabove while not substantially adversely affecting the properties of the compositions into which they are incorporated. Thus, such liquids can be used, either alone or in conjunction with the essential oils, to incorporate additional flavoring agents in those embodiments of the invention where this is desired.

The present conditioning compositions into which the essential oils are incorporated are advantageous over conventional conditioning compositions in that they have either a lesser unpleasant flavor than their conventional counterparts, or may even have a pleasant flavor relative to conventional compositions. Surprisingly, utilizing an essential oil to provide these advantageous sensory properties to conventional conditioning compositions does not adversely affect the ability of a tooth surface conditioned with the inventive compositions to bond with other dental materials. As a result of these beneficial properties of the conditioning composition, the conditioning composition of the present invention may advantageously be used to condition the surface of a tooth to which a free radically polymerizable dental material is to be adhered, and thus the present invention provides both a method of conditioning a tooth surface, and a method of adhering a free radically polymerizable dental material to a conditioned tooth surface.

More specifically, the methods of the present invention involve applying a conditioning composition comprising an essential oil to a tooth surface to which the free radically polymerizable dental material is to be applied in an amount effective to etch at least a portion of the tooth surface. The conditioning composition may be applied to the tooth surface that is desirably conditioned by any conventional method known to those of ordinary skill in the art. That is, the inclusion of the essential oil into conventional conditioning compositions beneficially does not substantially alter the handling properties of the conditioning composition so that special equipment would be required to apply the conditioning compositions of the present invention. A free radically polymerizable dental material may then be applied to the etched tooth surface and caused to harden, or cure. Advantageously, the bond strength that may be achieved between a tooth surface treated with the conditioning composition of the present invention and a free-radically curable dental material is comparable to that that is achievable when a conventional conditioning composition is utilized to treat a tooth surface, as is shown in Examples 1 and 2, hereinbelow.

Any desired free radically polymerizable dental material may be applied to the conditioned tooth surface. That is, because any residual amounts of the essential oils will not affect the ability of these types of materials to form substantially permanent bonds with the conditioned tooth surface, the particular free radically polymerizable dental material applied is not particularly restricted. Such dental materials are well known and easily recognized by those of ordinary skill in the art and include, for example resin composite tooth restorative materials, including but not limited to flowable composites, packable or condensable composites, hybrid composites, microfilled composites and continuum filled composites, as well as compomers, pit and fissure sealants, orthodontic adhesives and resin-based cements. Commercially available free radically polymerizable dental materials that may be bonded to a tooth surface conditioned according to the present invention, but are not limited to Silux Plus (microfilled composite, 3M, St Paul, Minn.). HRV Herculite (hybrid composite, Kerr, Orange, Calif.), Restorative Z 100 (continuum filled, 3M, St Paul, Minn.), Aeliteflo (flowable composite, Bisco, Schaumburg, Ill.), Alert (packable or condensable composite, Jeneric/Pentron, Wallingford, Conn.), Compoglass (compomer, Ivoclar North America Inc, Amherst, N.Y.), Aeliteseal (pit and fissure sealant, Bisco, Schaumburg, Ill.). Cure-on-Touch (orthodontic adhesive, Scientific Pharmaceuticals, Pomona, Calif.), and Imperva Dual Activated Resin Cement (resin-based cement, Shofu Dental Corporation, Menlo Park, Calif.)

The present invention will be described below with reference to the following representative examples, wherein bond strength was determined as follows.

EXAMPLE 1

Bonding to Enamel

Shear bond strength to tooth enamel was determined. Extracted human teeth were used. Each tooth was sectioned to give a portion of the tooth with an intact enamel surface. Each tooth portion was embedded in an autopolymerizing acrylic resin cement in an aluminum ring, to leave the enamel surface exposed. The surface were then polished wet under 5 lb pressure on 600 grit carborundum paper for 30 seconds in an automatic polishing machine (Buehler Ecomet 3 with Automat 2 powerhead, Buehler Ltd, Lake Bluff, Ill.). Each specimen was etched for 20 seconds, washed with distilled water for 20 seconds, then dried thoroughly by air from a pressure line. To each surface, a cylinder of resin composite was applied, which was cured by the application of visible light of wavelength approximately 470–480 nm and intensity 450 mW/square centimeter (Visilux 2 curing light, 3M, St Paul, Minn.). Specimens were stored in water at 37° C. for 24 hours in distilled water prior to testing. Testing was carried out using a shear bond testing rig and described and illustrated by Holtan et al (*Journal of Dentistry*. vol 22, pages 92–96, 1994 April). The testing machine was Instron model 4204 (Instron, Canton, Mass.), used at a rate of cross head movement of 1mm/min. There were three experimental groups, and 5 specimens per group.

Group 1, using standard continuum filled composite (Restorative Z100, 3M, St Paul, Minn.) and standard Scotchbond etchant (3M, St Paul, Minn.)—control group. Mean shear bond strength was 19.6 MPa Group 2, using the same composite as Group 1, but using modified etchant. This etchant was Scotchbond etchant (3M, St Paul, Minn.) altered so as to contain 15% by weight soybean oil. Mean shear bond strength 17.3 Mpa Group 3, using the unmodified etchant (Scotchbond etchant, 3M, St Paul) but with restorative Z100 (3M, St Paul, Minn.) modified so as to contain 2 per cent by weight soy bean oil. Mean bond strength 17.1 MPa.

Statistical tests (ANOVA) showed no significant difference between the data for the three groups (p>0.05).

EXAMPLE 2

Bonding to Dentin

Impacted third molar teeth that had been surgically extracted no longer than one month were used. The teeth were sectioned to expose dentin, and then mounted in aluminum rings, and polished, as in Example 1. The exposed dentin surfaces were conditioned with an etchant for 15 seconds, washed with distilled water for 20 seconds, then gently blotted to leave the dentin moist. Two coats of Single Bond adhesive (3M, St Paul, Minn.) were applied and gently air dried to avoid excessive thinning of the liquid adhesive. The adhesive was cured by visible light for 10 seconds, using the curing light described in Example 1. Then the resin composite (Restorative Z100, 3M, St Paul, Minn.) was applied to the surfaces with adhesive, to form a cylinder of composite. The composite was cured for 40 seconds, using the same light curing unit. Specimens were stored in distilled water at 37° C. for 24 hours. The testing rig and machine, and testing conditions were as described in Example 1. There were two experimental groups, and 10 samples per group.

Group 1 (control), using Scotchbond etchant (3M, St Paul, Minn.) as supplied. Shear bond strength 21.2 MPa Group 2, using Scotchbond etchant (3M, St Paul, Minn.) modified so as to contain 15% by weight of soybean oil. Shear bond strength, 20.4 Mpa.

Statistical testing (t-test) showed no significant difference between the two groups.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A method for treating a tooth by forming a substantially permanent bond between the tooth and a free radically polymerizable dental material comprising:
   (a) applying a conditioning composition comprising an essential oil to a tooth surface to which the free radically polymerizable dental material is to be applied in an amount effective to etch at least a portion of the tooth surface;
   (b) applying the free radically polymerizable dental material to the etched tooth surface; and
   (c) causing the free radically polymerizable dental material to harden.

2. The method of claim 1, wherein the essential oil is selected from the group consisting of soybean oil, safflower oil, sesame oil, olive oil, sunflower oil, canola oil, walnut oil, peanut oil, orange oil, eucalyptus oil, cod liver oil, castor oil or a combination thereof.

3. The method of claim 1, wherein the essential oil is present in the conditioning composition in an amount of from about 1 weight percent to about 35 weight percent, based upon the total weight of the conditioning composition.

4. The method of claim 3, wherein the essential oil is present in the conditioning composition in an amount of from about 10 weight percent to about 20 weight percent, based upon the total weight of the conditioning composition.

5. The method of claim 4, wherein the essential oil is present in the conditioning composition in an amount of from about 13 weight percent to about 17 weight percent, based upon the total weight of the conditioning composition.

6. The method of claim 1, wherein the formed bond has a bond strength of at least 13 MPa.

7. The method of claim 6, wherein the formed bond has a bond strength of from about 15 MPa to about 35 MPa.

8. The method of claim 1 wherein the conditioning composition further comprises flavoring agent.

9. The method of claim 2 wherein the flavoring agent is selected from the group consisting of a cherry flavor, a strawberry flavor, a blueberry flavor, a watermelon flavor, an orange flavor, a lemon flavor, a lime flavor, a raspberry flavor, an apple flavor, a grape flavor, a cranberry flavor, a coconut flavor, a caramel flavor, a banana flavor, a tangerine flavor, a pineapple flavor, a bubble gum flavor, an almond flavor, a hazelnut flavor, and mixtures thereof.

10. The method of claim 8 wherein the conditioning composition contains soy bean oil as a carrier for flavoring agent.

11. The method of claim 8 wherein the conditioning composition comprises phosphoric acid, soy bean oil as a carrier for a flavoring agent, and wherein the flavoring agent is selected from the group consisting of a cherry flavor, a strawberry flavor, a blueberry flavor, a watermelon flavor, an orange flavor, a lemon flavor, a lime flavor, a raspberry flavor, an apple flavor, a grape flavor, a cranberry flavor, a coconut flavor, a caramel flavor, a banana flavor, a tangerine flavor, a pineapple flavor, a bubble gum flavor, an almond flavor, a hazelnut flavor, and mixtures thereof.

12. A method of conditioning a tooth surface for application of a free radically polymerizable dental material comprising applying a conditioning composition comprising an essential oil to the surface to which the dental material is to be applied in an amount effective to etch at least a portion of the tooth surface.

13. The method of claim 12, wherein the essential oil is selected from the group consisting of soybean oil, safflower oil, sesame oil, olive oil, sunflower oil, canola oil, walnut oil, peanut oil, orange oil, eucalyptus oil, cod liver oil, castor oil or a combination thereof.

14. The method of claim 12 wherein the conditioning composition further comprises a flavoring agent.

15. The method of claim 14 wherein the conditioning composition contains soy bean oil as a carrier for flavoring agent.

16. The method of claim 15 wherein the flavoring agent is selected from the group consisting of a cherry flavor, a strawberry flavor, a blueberry flavor, a watermelon flavor, an orange flavor, a lemon flavor, a lime flavor, a raspberry flavor, an apple flavor, a grape flavor, a cranberry flavor, a coconut flavor, a caramel flavor; a banana flavor, a tangerine flavor, a pineapple flavor, a bubble gum flavor, an almond flavor, a hazelnut flavor, and mixtures thereof.

17. The method of claim 14 wherein the conditioning composition comprises phosphoric acid, and soy bear oil as a carrier for flavoring agent.

18. A method for treating a tooth by forming a substantially permanent bond between the tooth and a free radically polymerizable dental material, the method comprising:
   (a) applying a conditioning composition comprising essential oil to a tooth surface to which the free radically polymerizable dental material is to be applied, in an amount effective to etch at least a portion of the tooth surface, the conditioning composition comprising phosphoric acid, from about 1 to about 35 weight percent soy bean oil as a carrier for a flavoring agent, based on the total weight of the conditioning composition, and flavoring agent,
   (b) applying the free radically polymerizable dental material to the etched tooth surface; and
   (c) causing the free radically polymerizable dental material to harden.

19. The method of claim 18 wherein the conditioning composition comprises from about 13 to about 17 weight percent soybean oil, based on the total weight of the conditioning composition, and the flavoring agent is selected from the group consisting of a cherry flavor, a strawberry flavor, a blueberry flavor, a watermelon flavor, an orange flavor, a lemon flavor, a lime flavor, a raspberry flavor, an apple flavor, a grape flavor, a cranberry flavor, a coconut flavor, a caramel flavor, a banana flavor, a tangerine flavor, a pineapple flavor, a bubble gum flavor, an almond flavor, a hazelnut flavor, and mixtures thereof.

* * * * *

UNITED STATES PATENT AND TRADEMARK OFFICE
CERTIFICATE OF CORRECTION

PATENT NO.     : 6,419,904 B1
DATED          : July 16, 2002
INVENTOR(S)    : Combe et al.

It is certified that error appears in the above-identified patent and that said Letters Patent is hereby corrected as shown below:

<u>Title page,</u>
Title, should be -- METHODS FOR USING FLAVORED TOOTH CONDITIONING COMPOSITIONS TO CONDITION A TOOTH SURFACE --.

<u>Column 9,</u>
Line 58, "claim 2" should be -- claim 8 --.

<u>Column 10,</u>
Line 36, "soy bear oil" should be -- soy bean oil --.

Signed and Sealed this

Fifth Day of November, 2002

Attest:

Attesting Officer

JAMES E. ROGAN
Director of the United States Patent and Trademark Office